(12) United States Patent
Palmieri, III

(10) Patent No.: US 9,514,726 B2
(45) Date of Patent: Dec. 6, 2016

(54) ELECTROMAGNETIC TRANSDUCERS AND METHODS OF MAKING

(71) Applicant: Duneland Labs, LLC, Chicago, IL (US)

(72) Inventor: F. Robert Palmieri, III, Chicago, IL (US)

(73) Assignee: Duneland Labs, LLC, Chicago, IL (US)

( * ) Notice: Subject to any disclaimer, the term of this patent is extended or adjusted under 35 U.S.C. 154(b) by 0 days.

(21) Appl. No.: 15/050,134

(22) Filed: Feb. 22, 2016

(65) Prior Publication Data

US 2016/0247497 A1 Aug. 25, 2016

Related U.S. Application Data

(60) Provisional application No. 62/118,545, filed on Feb. 20, 2015.

(51) Int. Cl.
  *G10H 3/18* (2006.01)
  *G01N 29/24* (2006.01)
  *H01F 7/02* (2006.01)

(52) U.S. Cl.
  CPC .......... *G10H 3/181* (2013.01); *G01N 29/2412* (2013.01); *H01F 7/0205* (2013.01); *G01N 2291/101* (2013.01)

(58) Field of Classification Search
  CPC ................. G10H 3/181; G01N 29/2412; G01N 2291/101; H01F 7/0205
  USPC .................................................... 84/726–728
  See application file for complete search history.

(56) References Cited

U.S. PATENT DOCUMENTS

| | | | | |
|---|---|---|---|---|
| 4,442,749 A * | 4/1984 | DiMarzio | ............... | G10H 3/181 84/728 |
| 4,524,667 A * | 6/1985 | Duncan | .................. | G10H 3/181 84/728 |
| 4,809,578 A * | 3/1989 | Lace, Jr. | ................ | G10H 3/181 84/726 |
| 5,221,805 A * | 6/1993 | Lace | ...................... | G10H 3/181 84/726 |
| 5,438,158 A * | 8/1995 | Riboloff | ................... | G10D 1/08 84/267 |
| 5,767,431 A * | 6/1998 | Khanagov | .............. | G10H 3/181 84/726 |
| 5,831,196 A * | 11/1998 | Khanagov | .............. | G10H 3/181 84/726 |
| 5,894,101 A * | 4/1999 | Damm | ................... | G10H 3/181 84/723 |
| 6,897,369 B1 * | 5/2005 | Lace | ...................... | G10H 3/181 84/727 |

(Continued)

*Primary Examiner* — Jeffrey Donels
(74) *Attorney, Agent, or Firm* — Hartman Global IP Law; Gary M. Hartman; Michael D. Winter

(57) ABSTRACT

Electromagnetic transducers suitable for a variety of uses, including but not limited to musical instrument pickups. Such a transducer has a primary loop formed by an electrically conductive strip having oppositely-disposed ends and a slot extending therebetween that defines electrically conductive runners. The strip is bent to define a first section of the primary loop that overlies a second section of the primary loop and a gap therebetween. The transducer further comprises sensing or driving elements that are at least partially received in the slot in the first section of the primary loop and a transformer electrically connected to the strip at one of the ends thereof opposite the first section of the primary loop.

20 Claims, 7 Drawing Sheets

(56) References Cited

U.S. PATENT DOCUMENTS 9,024,171 B2 * 5/2015 Lace ...................... G10H 3/181
                                                                               84/723

* cited by examiner

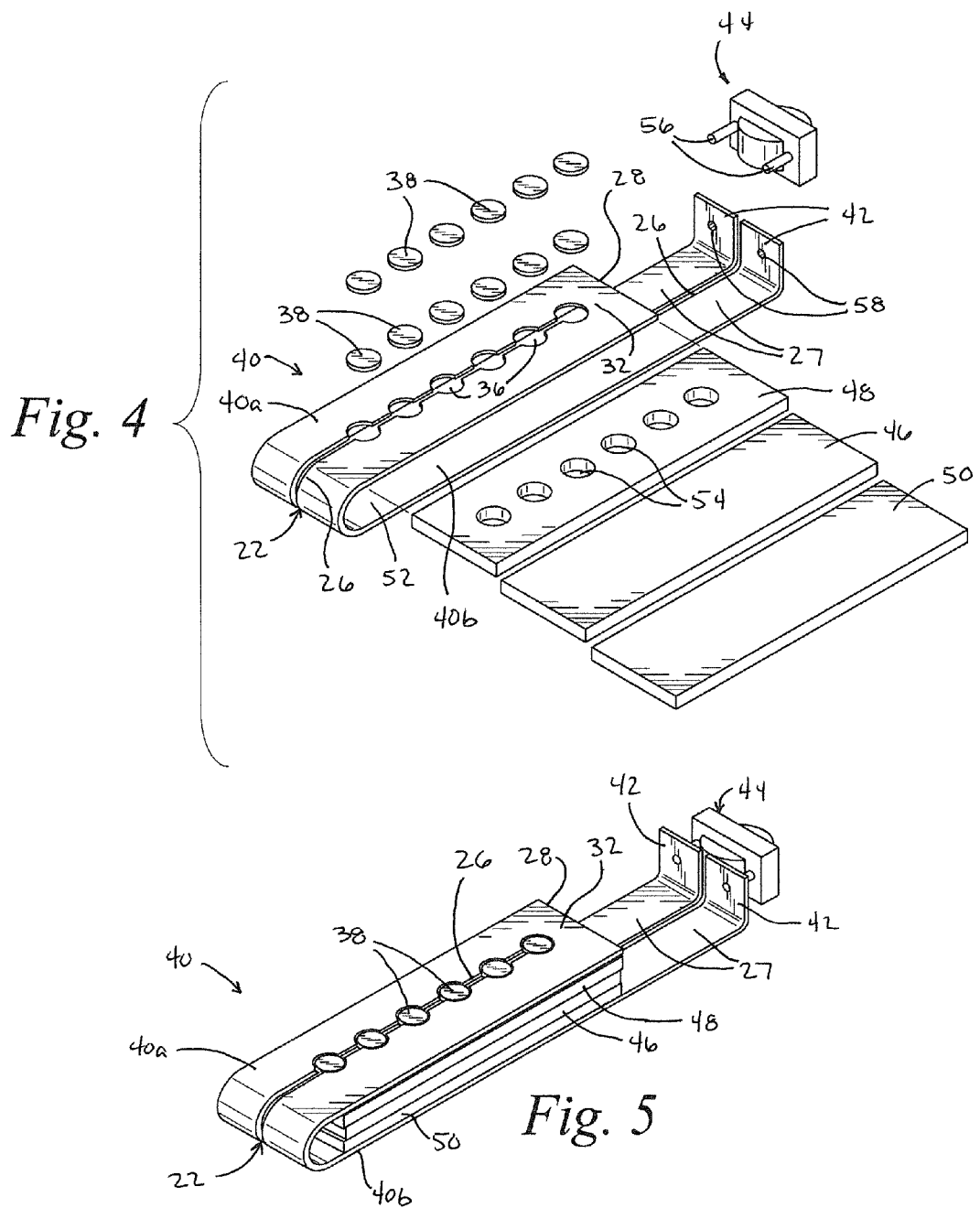

ELECTROMAGNETIC TRANSDUCERS AND METHODS OF MAKING

CROSS REFERENCE TO RELATED APPLICATIONS

This application claims the benefit of U.S. Provisional Application No. 62/118,545, filed Feb. 20, 2015, the contents of which are incorporated herein by reference.

BACKGROUND OF THE INVENTION

The present invention generally relates to electromagnetic transducers.

A single turn of conductive material can be simultaneously used as a sensing or driving element and the primary turn of a current transformer. Nonlimiting examples of devices that may utilize this principle include passive electromagnetic transducers of types used as musical instrument pickups, microphone elements, speaker elements, metal detectors, and sensors for automotive and industrial applications. Such devices can be configured to transform electrical power with a relatively high current to voltage ratio (low impedance) in their primary circuit into a similar power level in their secondary circuit, albeit with a high voltage to current ratio (high impedance.) As in the case of most passive transducers, this process can be inverted with respect to inputs and outputs.

There is an ongoing desire to be able to locate more conductive material of passive electromagnetic transducers in close proximity to an activity being sensed or driven. In so doing, it is also desirable to utilize relatively uncomplicated processes for producing passive transducers.

BRIEF DESCRIPTION OF THE INVENTION

The present invention provides electromagnetic transducers suitable for a variety of uses, including but not limited to musical instrument pickups, microphone elements, speaker elements, metal detectors, and sensors for automotive and industrial applications.

According to one aspect of the invention, an electromagnetic transducer comprises a primary loop formed by an electrically conductive strip having oppositely-disposed ends and a slot extending therebetween that defines electrically conductive runners. The strip is bent to define a first section of the primary loop that overlies a second section of the primary loop and a gap therebetween. The transducer further comprises sensing or driving elements that are at least partially received in the slot in the first section of the primary loop and a transformer electrically connected to the strip at one of the ends thereof opposite the first section of the primary loop.

Another aspect of the invention is a method of fabricating a transducer by forming an electrically conductive strip to have oppositely-disposed ends and a slot therebetween, bending the strip to define first and second sections of a primary loop so that the first section overlies the second section and a gap is therebetween, placing sensing or driving elements in the slot in the first section of the primary loop, and electrically connecting a transformer to the strip at one of the ends thereof opposite the first section of the primary loop.

Other aspects and advantages of this invention will be further appreciated from the following detailed description.

BRIEF DESCRIPTION OF THE DRAWINGS

FIGS. 4 and 5 represent exploded and assembly views, respectively, of the pickup of FIG. 1 produced from the strip of FIG. 3A.

DETAILED DESCRIPTION OF THE INVENTION

Figure 1:
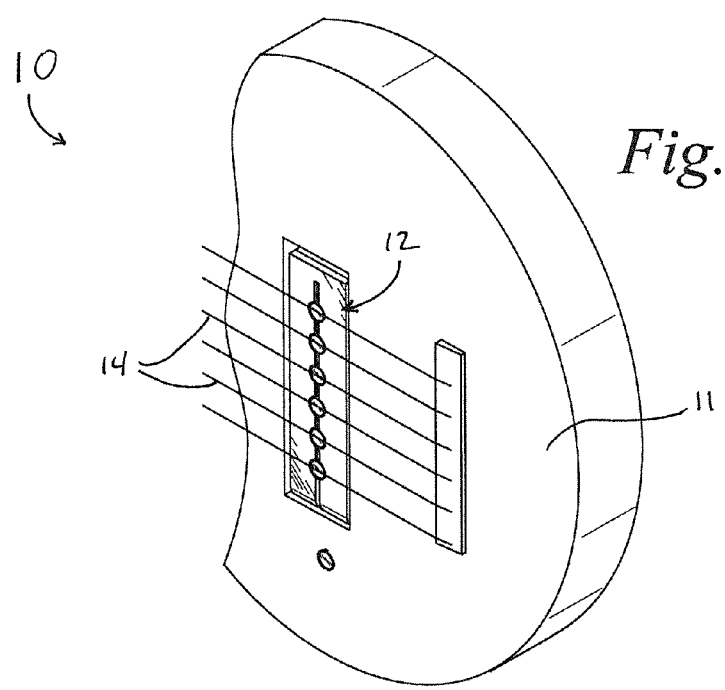
FIG. 1 is a fragmentary perspective view of an electric guitar showing an electric pickup in accordance with a nonlimiting embodiment of this invention.
Figure 8:
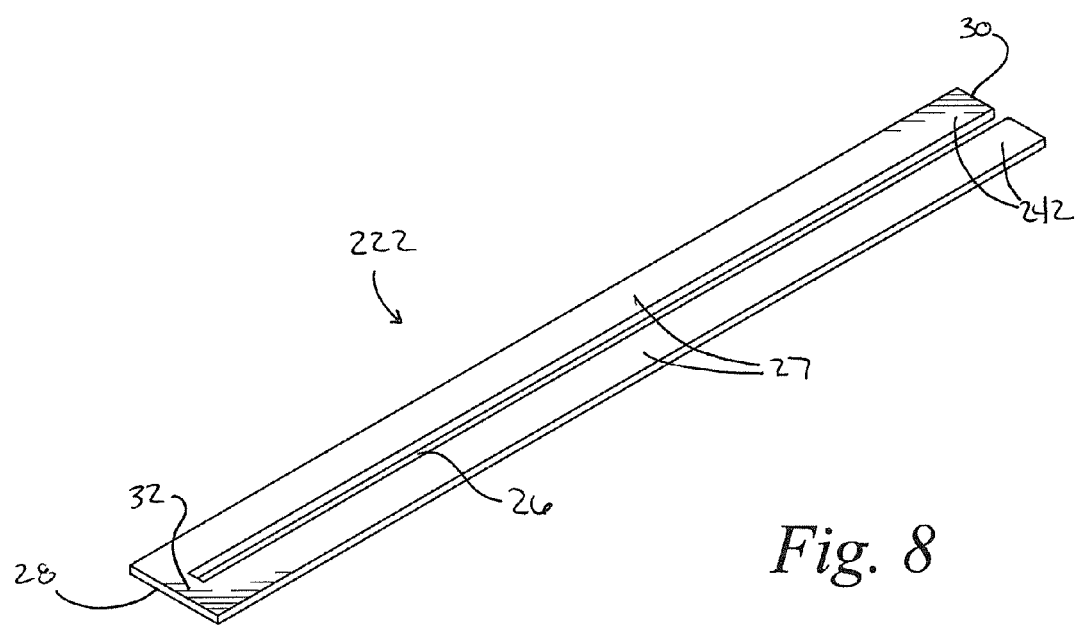
FIG. 8 is a perspective view of a second strip formed from the blank of FIG. 2.
Figure 10:
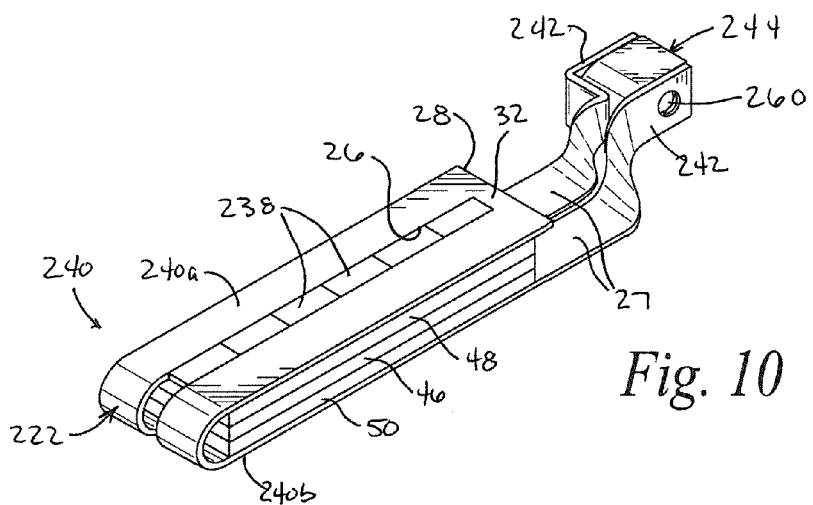

FIG. 1 represents a portion of an electric guitar 10 equipped with an electric pickup 12 in accordance with a nonlimiting embodiment depicted in FIG. 5, and FIGS. 8 and 10 represent two additional but nonlimiting embodiments of electric pickups 112 and 212 that are also within the scope of the invention. Although the invention will be described hereinafter in reference to an electric pickup, it will be appreciated that the teachings of the invention are more generally applicable to other types of electromagnetic transducers suitable for a variety of uses, including but not limited to a variety of musical instrument pickups, microphone elements, speaker elements, metal detectors, and sensors for automotive and industrial applications.

As with known pickups used with stringed instruments, the pickup 12 represented in FIG. 1 is adapted to sense the movement (vibration) of metal strings 14 of the guitar 10 and produce an electrical output in analog form. For this purpose, the pickup 12 is mounted to the body 11 of the guitar 12 in close proximity to the strings 14, for example, as a result of being recessed into the guitar body 11. Though FIG. 1 represents the pickup 12 as the sole pickup of the guitar 10, one or more additional pickups of any desired type could be employed in addition to the pickup 12.

The pickup 12 is based on the principle that a single turn of conductive material can simultaneously serve as a primary turn of a current transformer and as a sensing or driving element of a passive transducer. Such a transformer is generally adapted to transform an electrical power input with a relatively high current to voltage ratio (low impedance) in its primary circuit into an electrical power output having a similar power level at a relatively high voltage to current ratio (high impedance) in its secondary circuit. As in the case of most passive transducers, this process can be inverted with respect to the inputs and outputs, and this principle applies to both the transformer itself and the transducer system (including the below-described conductive strip and transformer elements) as a whole.

Figure 2:
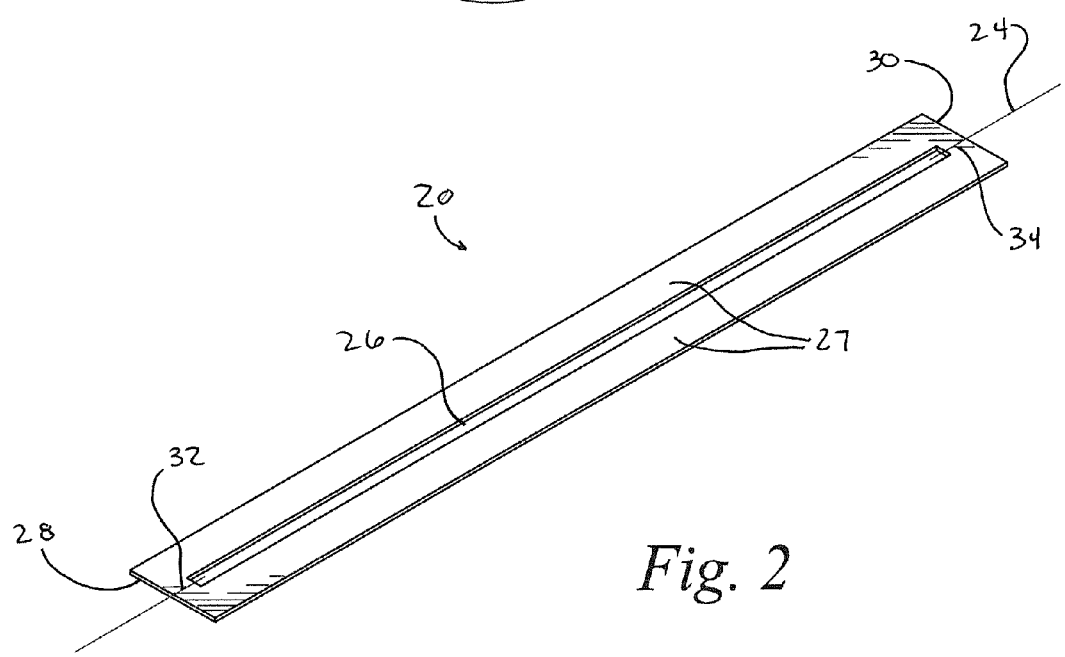
FIG. 2 is a perspective view of a blank from which the pickup of FIG. 1 can be fabricated.

FIG. 2 represents a blank 20 from which the pickup 12 can be fabricated. The blank 20 can be formed of an electrically conductive material (copper, as a nonlimiting example) and is represented as a flat rectangular member that can be a single homogeneous piece, a laminate, or other solid construction. An optional but decorative example is mokume-gane (mokume-game), which is a mixed-metal laminate capable of having distinctive layered patterns. The blank 20 is represented as being symmetrical along a central axis 24 thereof, and has a slot 26 formed along its central axis 24 to define two parallel runners 27 along the length of the blank 20. The longitudinal lengths and lateral widths of the blank 20, slot 26, and runners 27 can be sized to achieve a balance of structural, functional, and aesthetic aspects of the pickup 12. For example, FIG. 2 depicts each runner 27 as having a rectangular cross-sectional shape whose thickness is less than the width of the slot 26 between the runners 27. The slot 26 of the blank 20 is not continuous through either longitudinal end 28 or 30 of the blank 20, so that bridges 32 and 34 of significant width (in the axial direction of the blank 20) are present at both ends 28 and 30, respectively, connecting the runners 27 and effectively closing the slot 26 from the perimeter of the blank 20. In this form, the blank 20 is an electrical conductor capable of establishing circulating current flow through the material of the runners 27 and bridges 32 and 34 surrounding the slot 26. As an alternative to a blank in the form of flat stock as represented in FIG. 2, a suitable blank may be in the form of a wire, for example, a wire blank of roughly square-shaped cross-section, a nonlimiting example of which will be discussed below in reference to FIGS. 11 and 12.

A flat low-inductance conductor formed by the blank 20 provides a distinct advantage over both wound coils and thicker solid conductors of similar cross-sectional area, in that more conductive material can be placed in close proximity to the activity being sensed (e.g., the vibrating strings 14 of FIG. 1) or being driven. The blank 20 is also well suited to allow for the use of bending as one of any number of fundamental forming processes that can be used to fabricate the pickup 12 of FIG. 1. The blank 20 also allows the pickup 12 (or other sensing or driving element that can be formed from the blank 20) to become a primary structural and aesthetic element, for example, the pickup 12 can have a decorative aspect if formed by a mokume-gane process.

As will be discussed below in reference to FIGS. 3A through 10, the blank 20 of FIG. 2 can be used to form a variety of different conductive strips for use in an electromagnetic transducer. For convenience, consistent reference numbers are used throughout the drawings to identify the same or functionally equivalent elements of the blank 20 that are retained in the strips discussed below in reference to FIGS. 3A through 10.

Figure 3A:
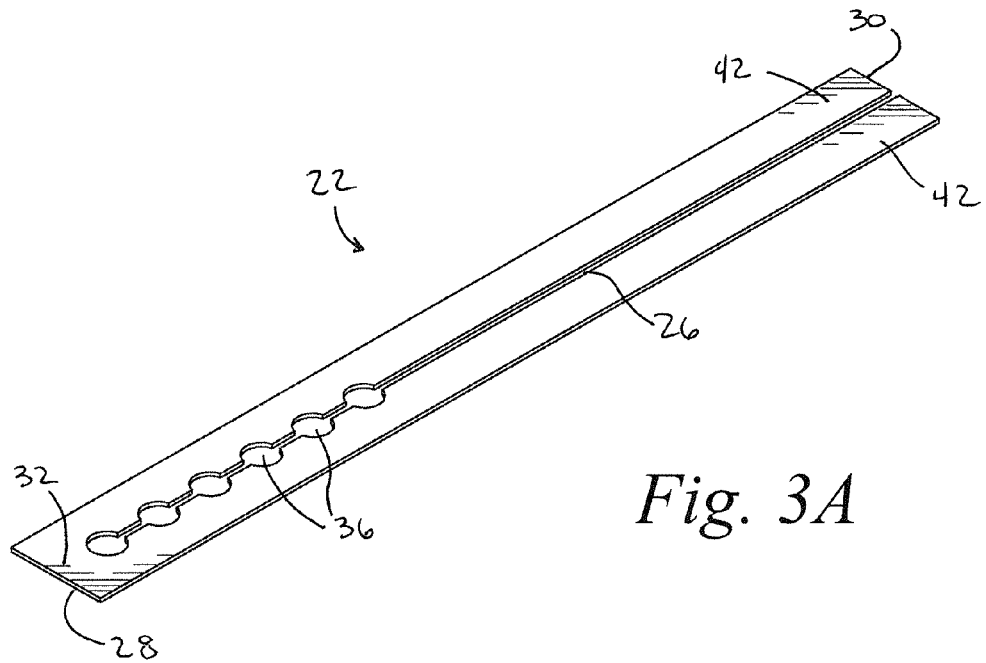
FIGS. 3A and 3B are perspective views of two strips formed from the blank of FIG. 2.
Figure 3B:
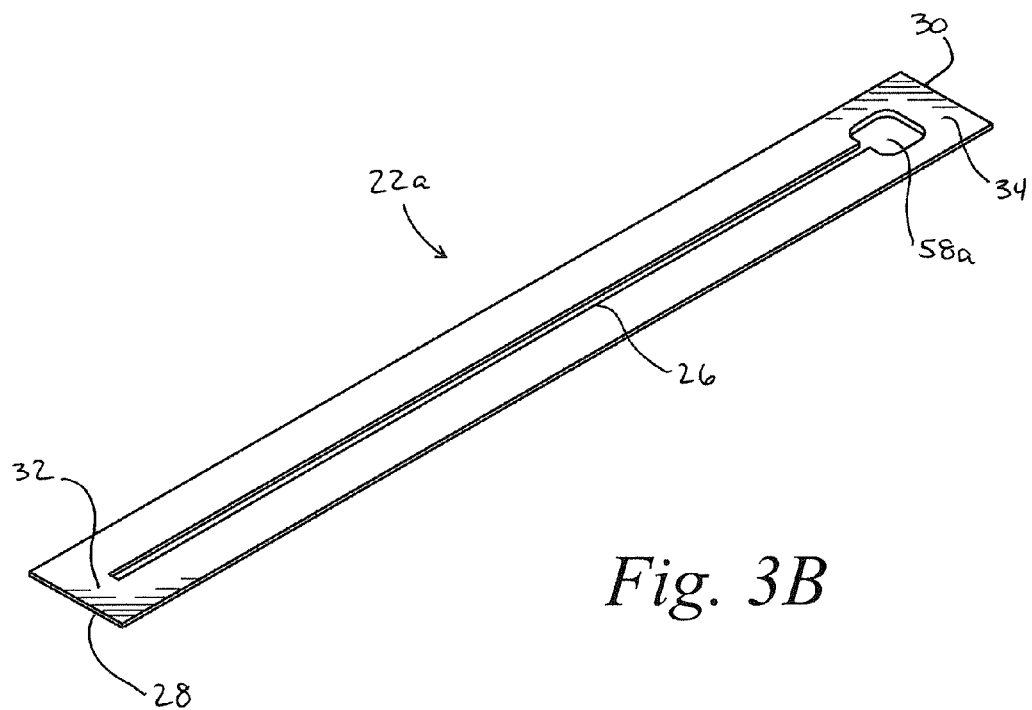

FIG. 3A represents the result of processing the blank 20 of FIG. 2 to form a conductive strip 22. In particular, the blank 20 has undergone further processing so that the strip 22 includes means for receiving and securing magnets and/or pole pieces, discussed in reference to FIGS. 4 and 5. In FIG. 3A, such means is in the form of apertures 36, which in FIGS. 4 and 5 receive and secure self-contained sensing or driving elements 38. In FIGS. 3A, 4 and 5, the apertures 36 are circular in shape to receive elements 38 that have complementary circular shapes, though other shapes are foreseeable. In addition, the apertures 36 can be seen to be interconnected by the slot 26. The elements 38 may be permanent magnets, flux-carrying pole pieces, or any combination thereof. FIG. 4 represents two sets of elements 38 being placed in the apertures 36, so that each aperture 36 receives a stack of two elements 38, though it is foreseeable that each aperture 36 could receive a single element 38 or more than two elements 38. In embodiments where an aperture 36 receives more than two elements 38, one of the elements 38 (e.g., an element 38 of either the upper or lower set in FIG. 4) could be a magnet and another could be a pole piece.

Either end 28 and 30 of the strip 22 can be bent, folded, and/or twisted to receive and secure a transformer. For example, in FIG. 3A a single bend has been formed in the end 30 of the blank 22 to receive a transformer (FIGS. 4 and 5). In addition, the bridge 34 has been eliminated by splitting or severing the end 30 of the blank 20, for example, by the continuation of the slot 26, with the resulting ends of the runners 27 defining two flanges 42 of the strip 22. FIG. 4 depicts the result of the strip 22 of FIG. 3A as having further undergone a bending operation to produce a "folded turn" and define a primary loop 40 having first and second sections 40a and 40b lying in separate planes that are approximately parallel to each other. The first section 40a overlies the second section 40b, is partially superimposed on the second section 40b, and defines a conductive sense or drive element of the primary loop 40. This configuration advantageously provides for nulling of ambient electromagnetic fields that may exist in the environment surrounding the primary loop 40. In particular, a magnetic field oriented so as to create a clockwise circulation of current in the first (top) section 40a of the loop 40 will simultaneously create a clockwise circulation of current in the second (lower) section 40b, and the two opposing currents will then cancel themselves in the loop 40 as a whole. This aspect can be most desirable, for example, if one-half of the loop 40 (the top section 40a) is adapted as an electromagnetic transducer by the introduction of permanent magnetic as sensing elements 38, as would be the intent for the pickup 12 depicted in FIG. 1.

An E-core transformer 44 is represented in FIG. 5 as being electrically coupled to the flanges 42 of the strip 22, which are optionally bent to accommodate the illustrated orientation of the transformer 44 relative to the primary loop 40. Finally, one or more optional magnetic, spacer, or support elements 46, 48 and 50 are represented as being installed in the space or gap 52 between the first and second sections 40a and 40b of the primary loop 40. As a nonlimiting example, the center element 46 may be a field guide or permanent magnet separated from the sections 40a and 40b by the elements 48 and 50, which may be spacers or supports formed of an electrical insulating material. The element 48 nearest the first section 40a is represented as having optional apertures 54 that are complementary to the apertures 36 in the strip 22, enabling the element 48 to at least partially accommodate the elements 38. The inclusion of the apertures 54 in the element 48 enables the thickness of the element 48 to establish the positions of the elements 38, for example, flush with or recessed below the surface of the first section 40a of the primary loop 40. The thicknesses of the elements 48 and 50 can also be tailored to establish the relative position of a field guide (e.g., 46) within the gap 52. The elements 38, 46, 48 and 50 can be retained within the primary loop 40 in any suitable manner, e.g., adhesively, magnetically, with an interference fit or additional retention structures, etc. The elements 38 may be individually surrounded with insulating rings (not shown), which in addition to providing an electrical and/or electromagnetic insulative effect, may also be utilized as retention structures.

As evident from FIGS. 4 and 5, the original flat rectangular shape of the blank 20 is retained by the first (top) and second (lower) sections 40a and 40b of the primary loop 40, and the first and second sections 40a and 40b are therefore shown in FIGS. 4 and 5 as parallel to each other. As previously noted, the thin planar configuration of the first section 40a is particularly advantageous because it provides a low-inductance conductor capable of positioning a relatively large mass of conductive material in close proximity to the activity being sensed (e.g., the vibrating strings 14 of FIG. 1) or driven. The close proximity of the planar first section 40a to the activity being sensed or driven is also advantageous because of its ability to place the functional electromagnetic (sensing/driving) elements 38 in such close proximity to the activity. With respect to its use as a pickup 12, such a capability is significant in comparison to conventional multi-turn solenoid coils.

The general concept described above in reference to the use of the blank 20 of FIG. 2 to form a primary loop can be adapted to provide a variety of primary loops having different configurations whose circulating currents can be coupled to a variety of different current transformers, the choice of which may be dependent on the configuration of the specific type of transformer employed. In FIGS. 4 and 5, the E-core transformer 44 features an internal primary turn, and terminals 56 of the transformer's primary turns (windings) are inserted into holes 58 formed in the flanges 42. The resulting connections can optionally be metallurgically joined (e.g., soldered) or mechanically joined by press-fitting if heated joinery is to be avoided. For an E-core transformer without an internal primary turn, the end 30 of the strip 22 can be shaped to accommodate the transformer's provided channel. In such a case, the primary loop 40 can be fabricated from a modified conductive strip 22a represented in FIG. 3B, in which case a single hole 58a intersected by the slot 26 can take the place of the holes 58 shown in FIG. 3A as the means for coupling the loop 40 to the E-core transformer (not shown).

Figure 6:
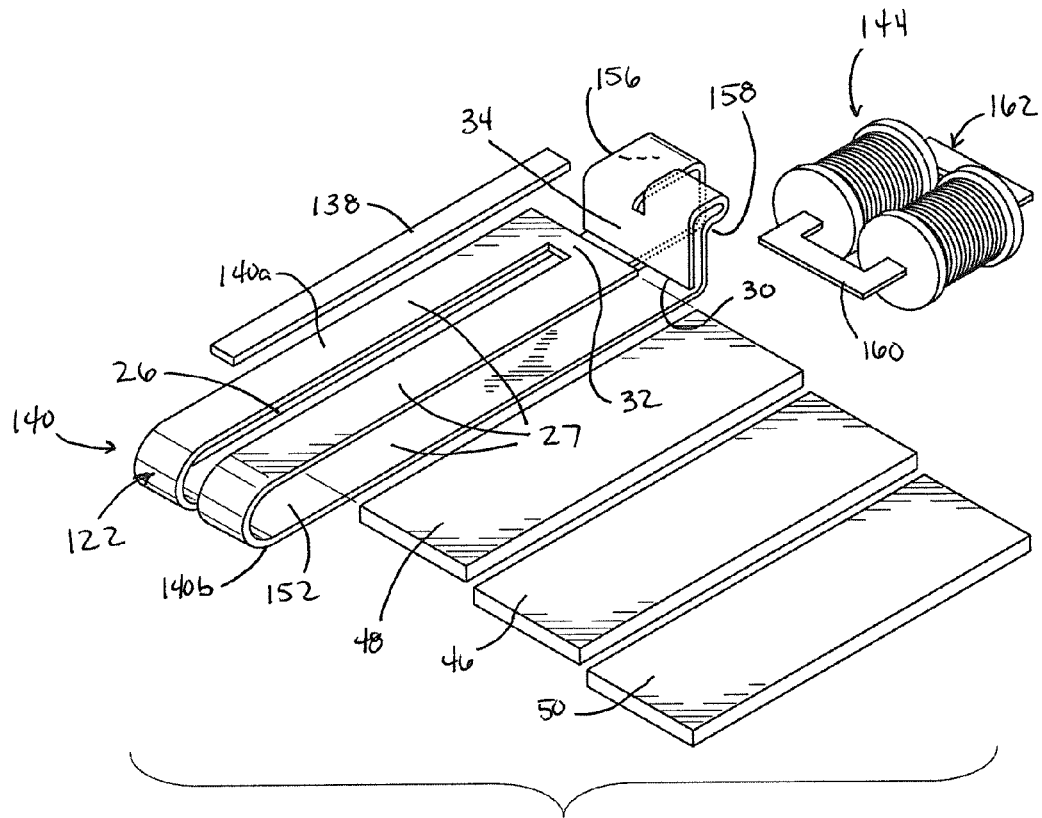
FIGS. 6 and 7 represent exploded and assembly views, respectively, of a pickup produced from the blank of FIG. 2 in accordance with another nonlimiting embodiment of this invention.
Figure 7:
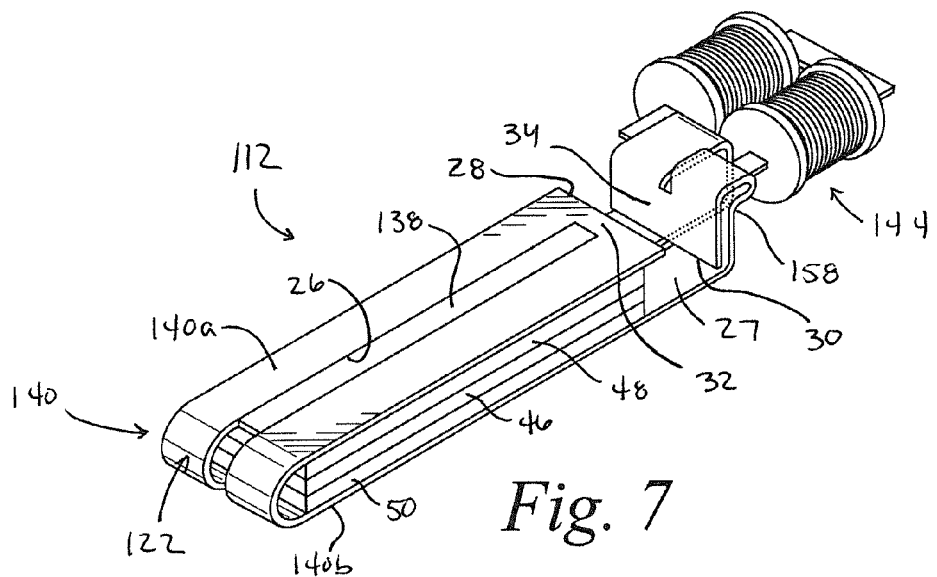

FIG. 7 represents another pickup 112 within the scope of the invention. In FIGS. 6 and 7, a C-core transformer 144 is assembled to a strip 122 in which the bridge 34 of the blank 20 (FIG. 2) has been retained. As seen in FIGS. 6 and 7, multiple bends have been formed in the end 30 of the strip 122. In particular, a tube 156 has been defined by curling the end 30 back on itself to leave a small gap between the bridge 34 and the runners 27 of the strip 122 on either side of the slot 26, and then crimping one of the runners 27 to define a crimp 158 so that the uncrimped runner 27 defines the tube 156 and allows for the placement of a bridging element 160 of the transformer core 162 within the tube 156, with the result that the bridging element 160 is encircled by the tube 156 as shown in FIG. 7. This configuration provides excellent magnetic coupling between the transformer core 162 and the conductive sense or drive element defined by the top section 140a of the primary loop 140 and a sensing/driving element 138 secured therein, while simultaneously allowing the transformer 144 to be magnetically shielded from undesirable electromagnetic and electrostatic fields without interfering with the sensing or driving abilities of the top section 140a of the primary loop 140. If desired, this configuration also allows the primary loop 140 to couple to conventional transformer cores without the necessity of introducing any welds or solder joints (with their attendant potential conductivity issues) into its continuous loop.

Figure 9:
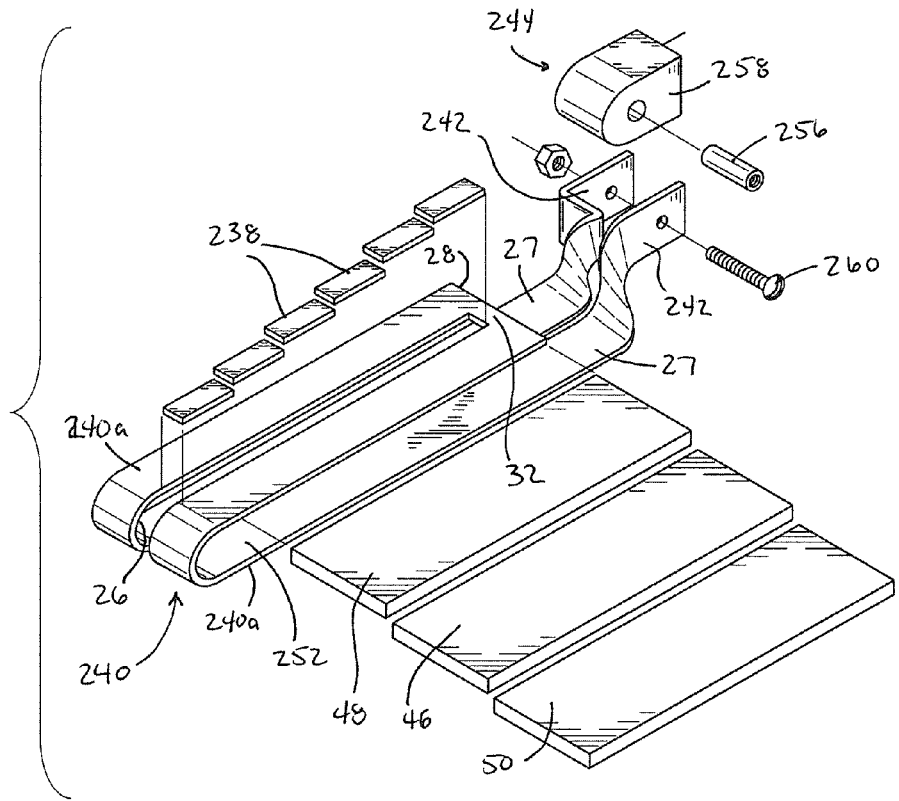
FIGS. 9 and 10 represent exploded and assembly views, respectively, of a pickup produced from the strip of FIG. 8 in accordance with another nonlimiting embodiment of this invention.

FIG. 10 represents a third pickup 212 within the scope of the invention. In FIGS. 9 and 10, a toroidal transformer 244 is employed as another method of achieving excellent magnetic coupling. This embodiment can make use of a strip 222 shown in FIG. 8, which is similar to the strip 22 in FIG. 3A with respect to elimination of the bridge 34 at the end 30 of the blank 20. However, the blank 20 has been further processed to form multiple bends and/or twists in the end 30 of the blank 22 to receive the transformer 244. The transformer 244 can be assembled by placing a piece of highly conductive material, such as a copper tube 256, in the center of a toroidal core 258. The ends 242 of the runners 27 separated by the slot 26 can be twisted and drilled to have the configuration shown in FIG. 9, then firmly affixed to the tube 256 with a fastener 260 as seen in FIG. 10. This configuration of a primary loop 240 shares the shielding advantages for the primary loop 140 described in reference to FIGS. 6 and 7 (e.g., the proximity of the sensing/driving elements 238 to the activity (e.g., strings 14) being sensed, as well as the valuable avoidance of metallurgically joining the loop 240 to the transformer 244 as described for the transformer 44 of FIGS. 3A and 4.

Figure 11:
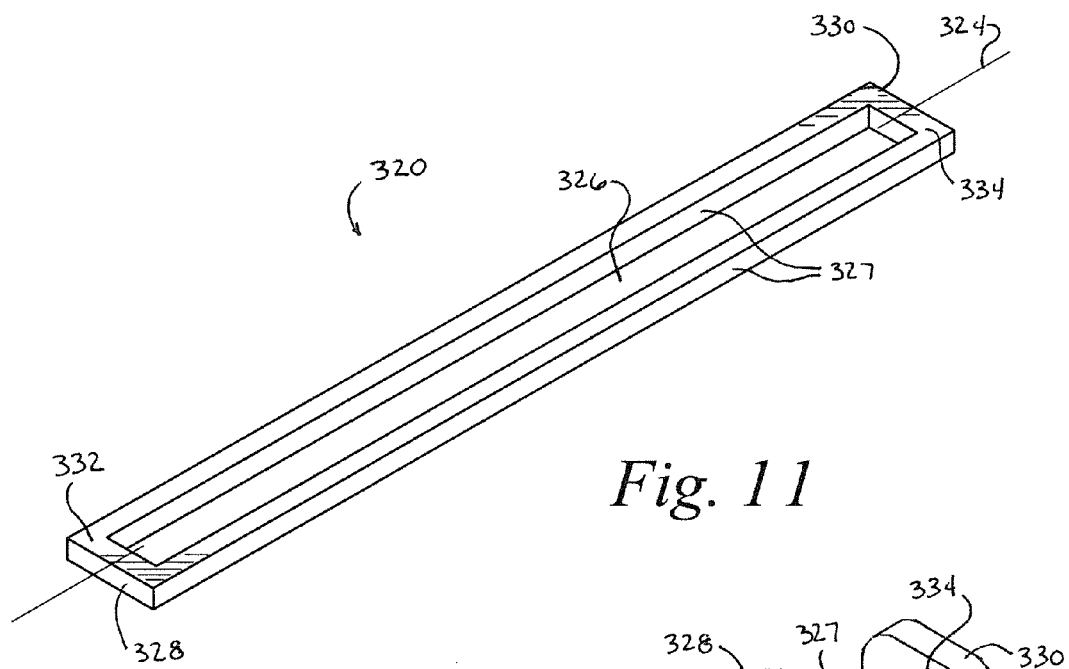
FIG. 11 is a perspective view of a wire blank from which a pickup can be fabricated in accordance with another nonlimiting embodiment of this invention.
Figure 12:
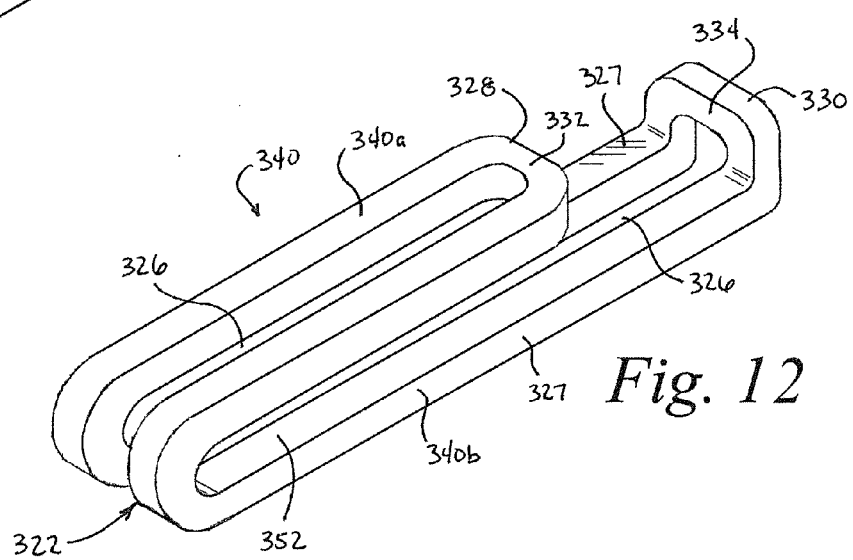
FIG. 12 represents a perspective view of a conductive strip produced by forming the wire blank of FIG. 11.

FIG. 11 represents an example of a wire blank 320 from which a conductive strip 322 can be formed as represented in FIG. 12. A nonlimiting example of a material for producing the blank 320 is a square cross-section copper wire (e.g., AWG 7, about 0.150×0.150 inch) whose ends have been welded or otherwise joined together. The blank 320 is generally similar to the blank 20 of FIG. 2 and the strip 322 is generally similar to the strip 222 as represented in FIG. 6 with respect to the presence of a rectangular-shaped slot 326 formed along its central axis 324 to define two parallel runners 327 along the length of the blank 320, and bridges 332 and 334 located at the longitudinal ends 328 and 330, respectively, of the blank 320. FIG. 12 represents that the blank 320 has undergone one or more forming steps to produce a "folded turn" that defines a primary loop 340 having first and second sections 340a and 340b lying in separate planes that are approximately parallel to each other, with the first section 340a overlying the second section 340b and being superimposed on a portion of the second section 340b to define a space or gap 352 therebetween. FIG. 12 also depicts the final configuration of the slot 326 as having a width that is approximately equal to the width and thickness of each runner 327, such that the strip 322 is capable of having a compact design.

Figure 13:
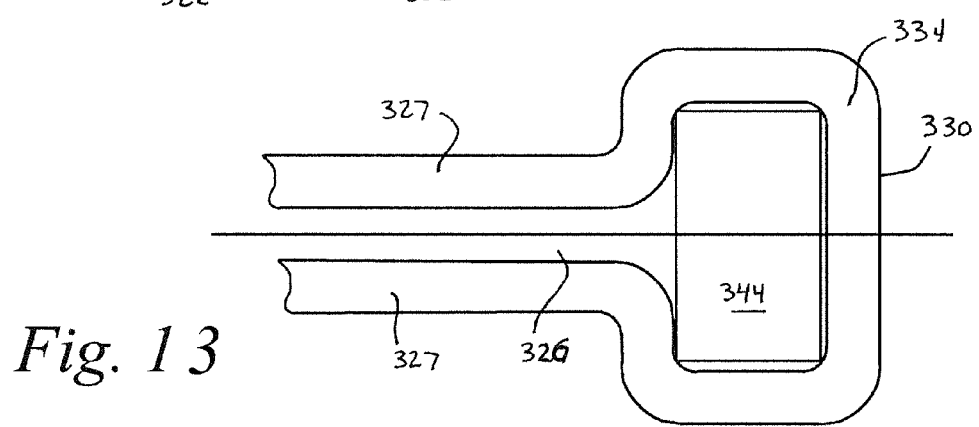
FIG. 13 represents a plan view of a conductive strip produced by forming the wire blank of FIG. 11 to have one end thereof that protrudes and/or wraps around a permeable core of a transformer to form a primary winding in the transformer.

Similar to the embodiment of FIG. 4, the end 330 of the blank 320 has been formed to have a single bend to accommodate a transformer (not shown) and orient the transformer relative to the primary loop 340. As should be evident from FIGS. 4-7, 9 and 10, a strip 322 produced from the wire blank 320 can be configured or modified to accept a variety of different transformers. For example, the end 330 of the blank 320 need not be bent at an angle of ninety degrees relative to the second section 340b as represented in FIG. 12, and instead the end 330 could be straight to couple with wires of the primary turn of a transformer. Another alternative represented in FIG. 13 is to form the end 330 of the blank 320 to protrude and/or wrap around the permeable core of a transformer 344, thereby forming a primary winding in the transformer 344. As with prior embodiments, one or more optional magnetic, spacer, or support elements (not shown) may be installed in the gap 352 between the first and second sections 340a and 340b of the primary loop 340. As evident from FIGS. 6, 7, 9 and 10, the configuration of the slot 326 can accommodate a variety of arrangements of magnetic sensing/driving elements (not shown), field guides, etc. The width of the slot 326 (the distance between the runners 327) can be varied, for example, closer together to more fully encircle the permeable core of a transformer and/or more intimately surround an array of sensing/driving elements (which can be of various sizes to address the characteristics of the action being sensed, for example, the individual strings 14 of FIG. 1). The wire blank 320 and strip 322 produced therefrom are capable of simultaneously increasing the proximity to both the action being sensed (e.g., the strings 14 of FIG. 1) and the sensing/driving elements, while also avoiding the use of more complicated bends or twists of the types represented in FIGS. 6, 7, 9 and 10.

As evident from the above, the above configurations may comprise a variety of arrangements of sensing/driving elements (e.g., permanent magnets and/or pole pieces 38, 138 and 238), field guides (e.g., element 46), passive structural members (e.g., elements 48 and 50 in FIGS. 4 through 7, 9 and 10), and strips 22, 122, 222 and 322, each of which may have a variety of configurations. One such aggregation is illustrated in FIG. 4, which shows the elements 38 as two sets of discs, which can be permanent magnets and/or flux-carrying pole pieces that are arranged so as to be either surrounded by or directly under the conductive sense or drive element formed by the top section 40a of the primary loop 40. The sensing/driving elements 38 can be supported by the elements 46, 48 and 50, which may comprise a field guide (e.g., element 46) and/or spacers or supports (e.g., elements 48 and 50). Other configurations can be realized with a single continuous magnetic element 138 (FIGS. 6 and 7) in place of multiple discs located at or under the surface of the top section 140a, or rectangular elements 238 (permanent magnets, pole pieces, or combinations thereof) arranged in a continuous row (FIGS. 9 and 10) within the slot 26/326. The elements 138 and 238 can be arranged as stacks of two or more elements, as is the case in FIG. 4. By utilizing some means for nonpermanently retaining the elements 38, 138 and 238 within the primary loop 40/340, e.g. magnetically, a user can easily swap magnets and pole pieces as the sensing/driving elements 38, 138, and 238 in the apertures 36 or slot 26/326. Another option is to omit the elements 38, 138 and 238, and instead utilize one or more of the elements 46, 48, and/or 50 within the gap 52, 152, 252 or 352 as a sensing/driving element of the primary loop 40, 140, 240, or 340.

While the invention has been described in terms of specific embodiments, it is apparent that other forms could be adopted by one skilled in the art. For example, the pickups 12, 112 and 212 could differ in appearance and construction from the embodiments shown in the Figures, the functions of each component of the pickups 12, 112, and 212 could be performed by components of different construction but capable of a similar (though not necessarily equivalent) function, and appropriate materials could be substituted for those noted. Accordingly, it should be understood that the invention is not limited to the specific embodiments illustrated in the Figures. It should also be understood that the phraseology and terminology employed above are for the purpose of disclosing the illustrated embodiments, and do not necessarily serve as limitations to the scope of the invention. Therefore, the scope of the invention is to be limited only by the following claims.

The invention claimed is:

1. An electromagnetic transducer comprising:
   a primary loop comprising an electrically conductive strip having oppositely-disposed ends and a slot extending therebetween that defines electrically conductive runners, the strip being bent to define a first section of the primary loop that overlies a second section of the primary loop and a gap therebetween;
   sensing or driving elements at least partially received in the slot in the first section of the primary loop, the sensing or driving elements being permanent magnets pole pieces, or combinations thereof; and
   a transformer electrically connected to the strip at one of the ends thereof opposite the first section of the primary loop.

2. The electromagnetic transducer according to claim 1, wherein the slot is continuous through one of the ends of the strip to define flanges at adjacent ends of the runners, and the transformer is electrically connected to the flanges.

3. The electromagnetic transducer according to claim 1, wherein the slot is not continuous through either of the ends of the strip to define bridges at adjacent ends of the runners, and the transformer is electrically connected to one of the bridges.

4. The electromagnetic transducer according to claim 1, wherein the slot is continuous through one of the ends of the strip to define flanges at adjacent ends of the runners, the flanges are spaced apart, and the transformer is electrically connected to the flanges and comprises a toroidal core disposed between the flanges.

5. The electromagnetic transducer according to claim 1, further comprising elements disposed within the gap of the primary loop, the elements comprising one or more field guides, spacers, supports, or combinations thereof.

6. The electromagnetic transducer according to claim 1, wherein the first section lies in a plane.

7. The electromagnetic transducer according to claim 1, wherein the second section lies in a second plane and is parallel to the first section.

8. The electromagnetic transducer according to claim 1, wherein the first section is superimposed on a portion of the second section to define the gap therebetween.

9. The electromagnetic transducer according to claim 1, wherein each of the runners has a rectangular cross-sectional shape having a thickness that is less than a width of the slot between the runners.

10. The electromagnetic transducer according to claim 9, wherein one of the ends of the strip defines flanges at adjacent ends of the runners, and the flanges are bent, fold, or twisted to receive and secure the transformer.

11. The electromagnetic transducer according to claim 1, wherein each of the runners has a square cross-sectional shape.

12. The electromagnetic transducer according to claim 11, wherein each of the runners has a thickness that is approximately equal to a width of the slot between the runners.

13. The electromagnetic transducer according to claim 11, wherein one of the ends of the strip defines a single bend at adjacent ends of the runners to receive and secure the transformer.

14. A guitar pickup comprising the electromagnetic transducer according to claim 1.

15. The electromagnetic transducer according to claim 14, wherein the first section lies in a plane and is in close proximity to strings of a guitar.

16. A sensor or driver for an industrial application comprising the electromagnetic transducer according to claim 1.

17. The electromagnetic transducer according to claim 16, wherein the first section lies in a plane and is in close proximity to an activity being sensed or driven.

18. A method of forming an electromagnetic transducer, the method comprising:

forming an electrically conductive strip to have oppositely-disposed ends and a slot therebetween;

bending the strip to define first and second sections of a primary loop so that the first section overlies the second section and a gap is therebetween;

placing sensing or driving elements in the slot in the first section of the primary loop, the sensing or driving elements being permanent magnets pole pieces, or combinations thereof; and electrically connecting a transformer to the strip at one of the ends thereof opposite the first section of the primary loop.

19. The method according to claim 18, further comprising forming at least one bend, fold, twist, or combinations thereof in one of the ends of the strip to receive or secure the transformer.

20. The method according to claim 18, wherein the strip is formed by bending a wire.

\* \* \* \* \*